US010406283B2

(12) United States Patent
Cane' et al.

(10) Patent No.: US 10,406,283 B2
(45) Date of Patent: Sep. 10, 2019

(54) CONNECTING ARRANGEMENT FOR CONNECTING A SYRINGE TO A PUMP FOR DRUG INFUSION

(71) Applicant: CANE' S.P.A., Rivoli (TO) (IT)

(72) Inventors: Claudio Cane', Rivoli (IT); Mario Cane', Rivoli (IT); Paolo Cane', Rivoli (IT)

(73) Assignee: CANE' S.P.A., Rivoli (TO) (IT)

( * ) Notice: Subject to any disclaimer, the term of this patent is extended or adjusted under 35 U.S.C. 154(b) by 0 days.

(21) Appl. No.: 15/597,774

(22) Filed: May 17, 2017

(65) Prior Publication Data

US 2017/0340810 A1    Nov. 30, 2017

(30) Foreign Application Priority Data

May 31, 2016   (IT) .................. 102016000056463

(51) Int. Cl.
*A61M 5/145* (2006.01)
*A61M 5/142* (2006.01)
(Continued)

(52) U.S. Cl.
CPC ........ *A61M 5/14566* (2013.01); *A61M 5/142* (2013.01); *A61M 5/14546* (2013.01);
(Continued)

(58) Field of Classification Search
CPC .... A61M 5/142; A61M 5/145; A61M 5/1452; A61M 5/14546; A61M 5/1456;
(Continued)

(56) References Cited

U.S. PATENT DOCUMENTS 5,944,694 A * 8/1999 Hitchins ........... A61M 5/14546
604/131
6,042,565 A   3/2000 Hirschman et al.
(Continued)

FOREIGN PATENT DOCUMENTS

EP   2394682 A1   12/2011
EP   2810673 A1   12/2014
EP   2832389 A1   2/2015

OTHER PUBLICATIONS

European Search Report and Opinion dated Oct. 24, 2017 issued in connection with counterpart co-pending European Patent Application No. 17171664.0 filed May 18, 2017.

*Primary Examiner* — Shefali D Patel
(74) *Attorney, Agent, or Firm* — Howson & Howson LLP

(57) ABSTRACT

An arrangement for connecting a syringe to an electromechanical pump for drug infusion is provided. The syringe comprises a syringe body having a first end for discharging a drug and a second end connected to the pump in a removable manner. An axially sliding plunger is housed in the syringe body for causing suction and injection of the drug through the first end. The pump comprises a pump body having a sliding rod that causes sliding of the plunger within the syringe body. The pump body has a collar axially extending around the sliding rod and provided with engaging elements. The syringe body has engaging elements arranged to cooperate with the engaging elements of the collar for firmly connecting the syringe to the pump. An annular flange extends radially around the syringe body. The flange cooperates with the collar to establish a tight sealing between the syringe body and the collar.

5 Claims, 8 Drawing Sheets

(51) Int. Cl.
*A61M 5/31* (2006.01)
*A61M 5/168* (2006.01)
(52) U.S. Cl.
CPC ... *A61M 5/168* (2013.01); *A61M 2005/14573* (2013.01); *A61M 2005/3123* (2013.01)
(58) Field of Classification Search
CPC .. A61M 5/14566; A61M 5/24; A61M 5/2422; A61M 5/31; A61M 5/3145; A61M 2005/14506; A61M 2005/14573; A61M 2005/2403; A61M 2005/2411; A61M 2005/2433; A61M 2005/2437; A61M 2005/244; A61M 2005/3123
See application file for complete search history.

(56) References Cited

U.S. PATENT DOCUMENTS

| | | | |
|---|---|---|---|
| 6,402,718 B1 | 6/2002 | Reilly et al. | |
| 6,569,127 B1 * | 5/2003 | Fago | A61M 5/14546 604/131 |
| 9,289,549 B2 | 3/2016 | Cane' | |
| 9,463,271 B2 | 10/2016 | Cane' | |
| 2013/0338635 A1 * | 12/2013 | O'Connor | A61M 5/16859 604/506 |
| 2015/0038906 A1 * | 2/2015 | Cane' | A61M 5/14566 604/152 |
| 2017/0035963 A1 | 2/2017 | Cane' | |

* cited by examiner

CONNECTING ARRANGEMENT FOR CONNECTING A SYRINGE TO A PUMP FOR DRUG INFUSION

CROSS REFERENCE TO RELATED APPLICATIONS

This application claims the benefit under 35 USC 119 of Italian Application No. 102016000056463, filed May 31, 2016.

BACKGROUND

The present invention concerns an arrangement for connecting a syringe to a drug infusion pump.

For drug infusion into the body of a living being, infusion pumps connected to a syringe in a removable manner are currently used.

The known syringes employed in drug infusion pumps typically are disposable syringes. Said syringes include a hollow cylindrical syringe body having a first, tapered open end, or front end, for discharging the drug. A second open end, or rear end, is generally surrounded by connecting means arranged to firmly connect the syringe to the infusion pump in a removable manner. A plunger is housed in the syringe body and is axially slidable for causing suction and injection of the drug through the first end. An example of syringe of the above kind, suitable for being connected to a drug infusion pump, is disclosed in EP 2810673 (A). The known syringes are generally filled before being connected to the infusion pump. Filling of the syringe is generally performed by sucking the drug through the front end of the syringe, by moving back the plunger by means of a control shaft. The shaft is removed before connecting the syringe to the pump.

In some applications, the syringe is commercialized already filled with drug.

The known infusion pumps are devices including a pump body internally housing the electromechanical members intended for pump operation. Said electromechanical members include a sliding rod partially projecting out of the pump body. The forward and backward movement of the rod relative to the pump body is driven by the electromechanical members of the pump. Said electromechanical members include an electric motor, generally supplied with power by a battery also housed within the pump body. The forward movement of the rod causes the forward movement of the plunger of a syringe connected to the pump and the resulting drug discharge from the front end of the syringe. Moreover, the pump body is generally externally equipped with connecting means arranged around the sliding rod and capable of receiving, in engagement configuration, the second end of the syringe body. An example of a drug infusion pump of such kind, suitable for use in association with a syringe, is disclosed in EP 2394682 (A).

As known, such pumps have the advantage of being particularly compact and of being wearable by the user during execution of the usual daily activities. Moreover, since the pump generally is self-powered by means of a battery, the user may wear the pump practically at any moment in the day, for instance also during care of personal hygiene, during open-air physical activity or, more simply, during usual outdoor displacements. In recent times, therefore, the need has arisen to make such pumps watertight, in order to enable use thereof in environments which are particularly wet or where a certain water amount exists, for instance in form of drops during a rainy day or under the shower.

In the known pumps of the kind discussed above, the rod projects out of the pump body through a suitable opening. That opening is one of the possible ways through which moisture and water can penetrate into the pump. Moisture possibly penetrating into the pump can cause damages to the electromechanical members, in particular to the printed circuits and the electronic components associated therewith, and can alter the pump operation, with even serious consequences for the user. In order to prevent that drawback, different measures are currently adopted in the known connecting arrangements for firmly connecting the syringe to the pump in a removable manner. For instance, the sliding rod is surrounded by an expansible bellows made of rubber, which should prevent moisture from penetrating into the pump. An exemplary solution to the above problem is also disclosed in EP 2832389 (A).

Yet, the prior art solutions have proved to be insufficiently reliable. Moreover, bellows expansion when the rod is moved forward to cause drug infusion gives rise to a vacuum condition within the bellows, contributing to suck air and hence moisture from the outside environment.

It is a first object of the invention to solve the problem of how to make the assembly consisting of the infusion pump and the syringe connected thereto watertight.

It is a second object of the invention to solve the above problem with means that are reliable and resistant even after a high number of infusions and consequent syringe replacements.

It is a further object of the invention to provide a solution to that problem, which can be industrially implemented in the pumps and the syringes with limited costs.

The above and other objects are achieved by means of the arrangement for connecting a syringe to a drug infusion pump as claimed in the appended claims.

SUMMARY

The arrangement according to the invention advantageously enables connecting a syringe, e.g. a disposable syringe or a pre-filled syringe, to a drug infusion pump, in particular an electromechanical pump, so as to make the assembly obtained in this manner substantially watertight.

The syringe is of a kind including a hollow cylindrical syringe body having a first, tapered open end, or front end, for discharging the drug, and a second open end, or rear end. The syringe body is surrounded by connecting means arranged to firmly connect the syringe to the infusion pump in a removable manner. A plunger is housed in the syringe body, which plunger is axially slidable in the syringe body and enables causing suction and injection of the drug through the front end of the syringe.

The pump is of a kind including a pump body internally housing the electromechanical members, which will not be further described since they are known to the skilled in the art. Said members include in particular a sliding rod. The sliding rod is driven by the electromechanical members of the pump and has in its front part a pushing member arranged to cooperate with the syringe plunger. The pushing member generally includes a blind body engaging the plunger body with or without interference, in a seat provided therein. Interference engagement between the pushing member and the plunger is generally necessary to prevent the phenomenon of the so-called free-flow of the drug, occurring when the plunger can axially slide forward, i.e. towards the front end, because of only hydrostatic pressure created within the syringe.

The pump body is further provided with connecting means arranged to receive the syringe body in an engaging configuration.

Advantageously, according to the invention, the connecting means provided on the pump body comprise a cylindrical collar axially extending around the sliding rod. Said collar defines a sealing end and is internally provided with engaging elements. Moreover, always according to the invention, the connecting means surrounding the syringe body comprise engaging elements arranged to cooperate with the engaging elements provided in the collar. Thanks to the cooperation between said engaging elements, it is possible to firmly connect the syringe to the pump in a removable manner. The connecting means surrounding the syringe body also comprise an annular flange, preferably integrated into the syringe body. The annular flange radially extends around the syringe body, in a plane that preferably is substantially perpendicular to the axis of the syringe body. Said flange is adapted to cooperate with the sealing end defined in the collar, in order to establish a tight sealing between the syringe body and the collar. Advantageously, thanks to such an arrangement, when the syringe is attached to the pump, any moisture that may be present in the surrounding environment outside the pump and the syringe attached thereto does not penetrate into the pump body.

In accordance with a preferred embodiment of the invention, the flange comprises a cross-section, i.e. a section lying in a plane parallel to the axis of the syringe when the flange lies in a plane perpendicular to the axis of the syringe body, having the shape of an overturned "U" when the syringe is oriented with its front end upwards. Consequently, an annular seat is defined in the flange and is adapted to receive the sealing portion of the collar when the syringe is attached to the pump.

Always in accordance with a preferred embodiment of the invention, the sealing portion of the collar comprises an annular groove radially open towards the outside. Said groove is adapted to receive a sealing gasket, e.g. an O-ring made of rubber or similar material.

The annular groove radially extends and the cross-section of the gasket is chosen so that said gasket partially radially extends outside the groove, in order to cooperate with the inner surface of the outer wall of the annular seat provided in the flange. When the syringe is attached to the pump, said gasket is pressed in its seat thereby determining the desired tight sealing between the syringe body and the pump collar. The gasket can be advantageously replaced when it is worn out.

In a variant of the invention, the gasket is lacking and the sealing between the syringe body and the collar is achieved only thanks to the interference between the respective materials, which typically will be plastics for the syringe and metal or plastics for the pump collar.

Preferably, the flange comprises an outer wall that, when the syringe is oriented with its front end upwards, ends at its bottom with a rounded edge. Advantageously, thanks to such an arrangement, premature wear of the sealing portion and the sealing gasket, if any, caused by interference with the flange when the syringe is attached to or detached from the pump, is avoided. Actually, it is to be remembered that, during the operating life of a pump, such operation is performed even thousands of times.

In accordance with a particular embodiment of the invention, the collar is provided with at least one radial channel putting the inside of the collar in communication with the outside. Preferably, said channel houses a porous element made of a material suitable for allowing passage of air and preventing passage of moisture. Advantageously, in this manner, the pressure inside the collar is maintained equal to the pressure in the external environment, where atmospheric pressure typically exists. Preferably, two diametrically opposite channels are provided.

The engaging elements provided in the connecting means of the syringe and of the pump preferably comprise respective elements of a bayonet-type coupling. Preferably, the engaging elements provided in the connecting means of the syringe are female elements, i.e. annular grooves formed in the outer wall of the syringe body, and the engaging elements provided in the connecting means of the collar are male elements, i.e. annular radial teeth projecting inside the collar. Preferably, two said elements are provided, which are diametrically opposite and extend over an arc of circumference of about 30°.

According to the invention, the length of the collar may vary depending on the applications. The length of the collar may be much shorter than the length of the syringe body, for instance about one fifth of the length of the syringe body, or it may be approximately the same as the length of the syringe body. In the first case, the syringe is substantially attached outside the pump body, whereas in the second case the collar substantially surrounds the whole of the syringe body. According to the invention, when the collar has a length close or equal to the length of the syringe body, it is preferable to provide the front end of the syringe body with a flange radially projecting towards the outside, in order to enable an easy grip on the syringe body when the syringe is attached to or detached from the pump body. Advantageously, the flange is preferably externally equipped with radial projections making grip thereof easier. Moreover, the pump body may be equipped with a projection capable of interfering with one or more teeth radially projecting outside the flange, in order to determine a stop point for the rotation of the syringe body when the syringe is attached to the pump, thereby ensuring a better sensation of proper connection in the user.

BRIEF DESCRIPTION OF THE DRAWINGS

Some preferred embodiments of the invention will be described by way of non-limiting example with reference to the accompanying figures, in which.

DETAILED DESCRIPTION

Figure 1:
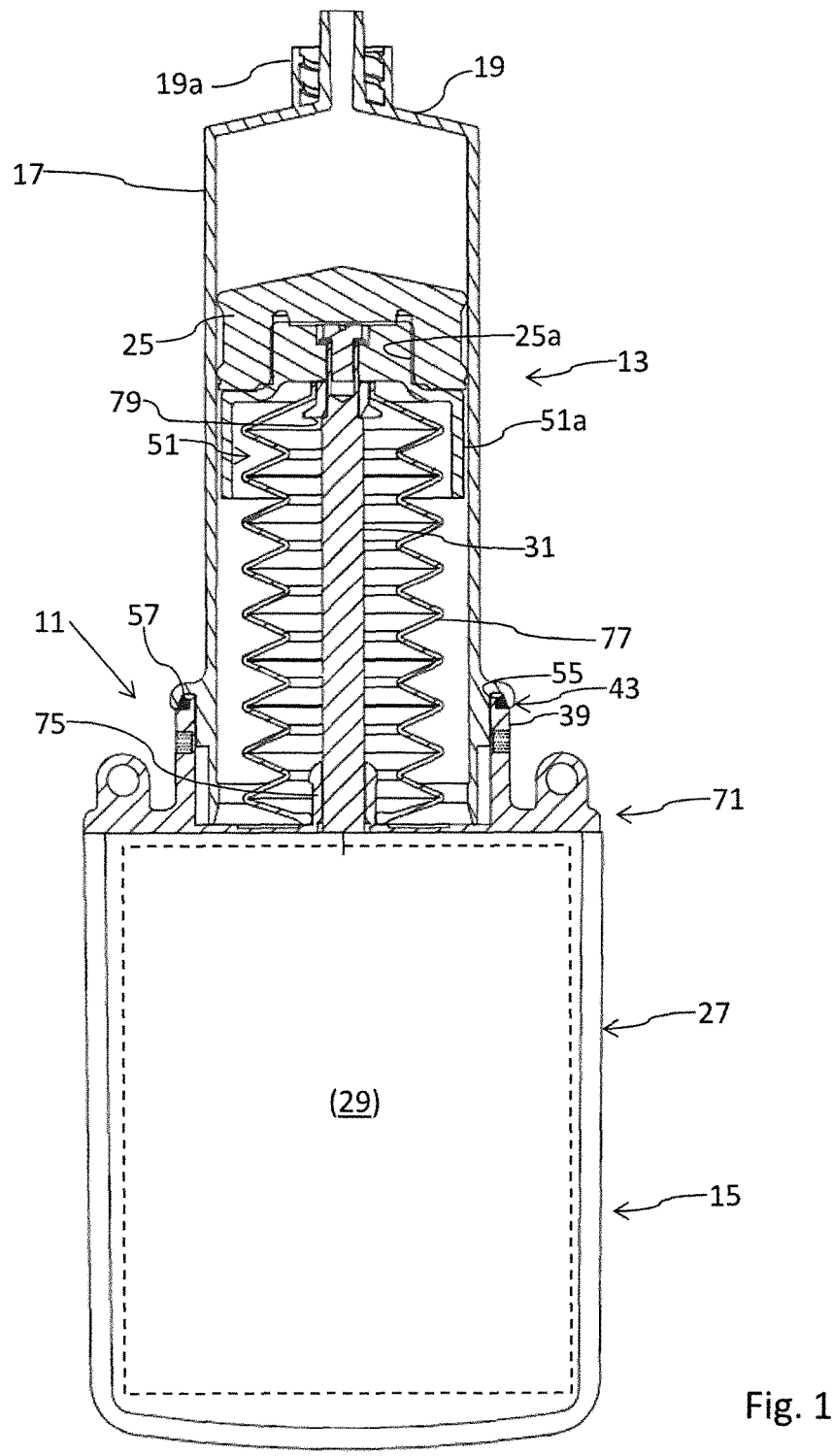
FIG. 1 is a longitudinal section of a pump equipped with a syringe connected to the pump through the arrangement of the invention, made in accordance with a first embodiment of the invention.
Figure 2:
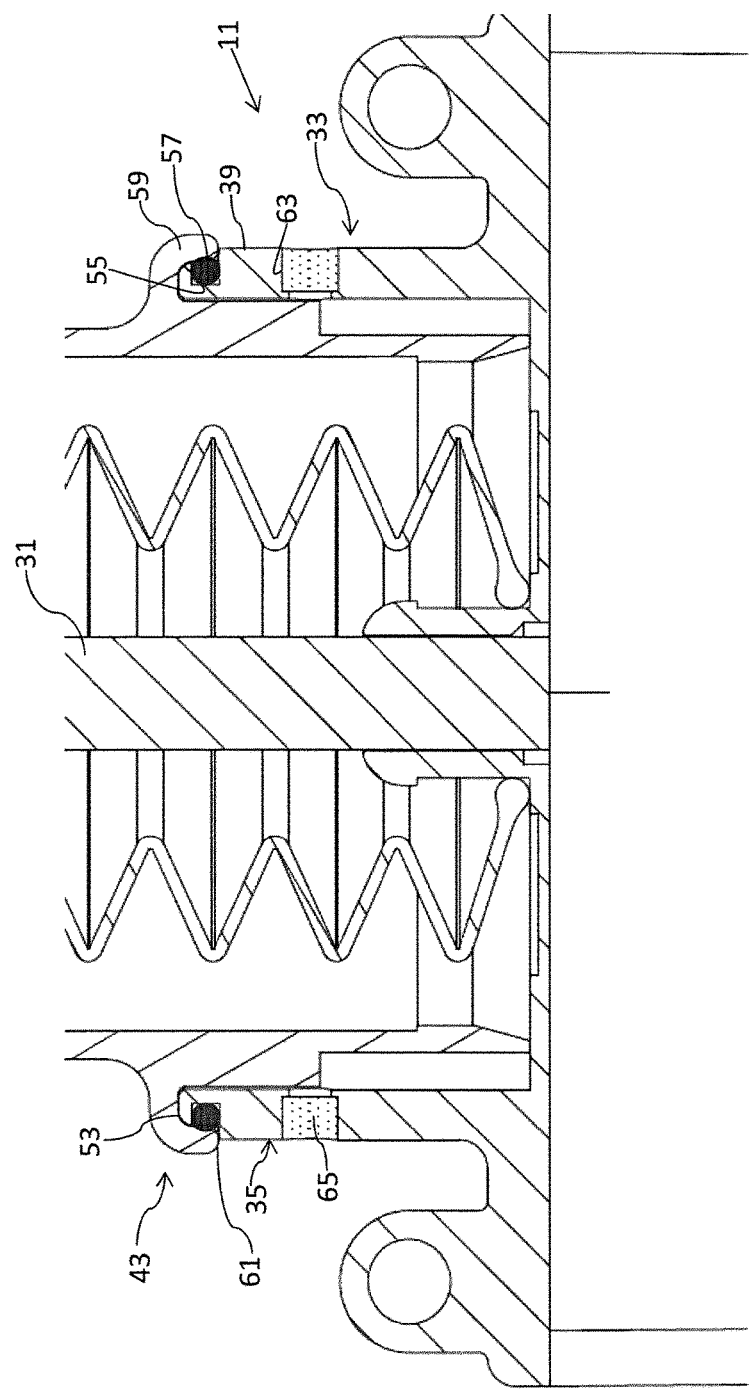
FIG. 2 is an enlarged view of a detail of FIG. 1.
Figure 3:
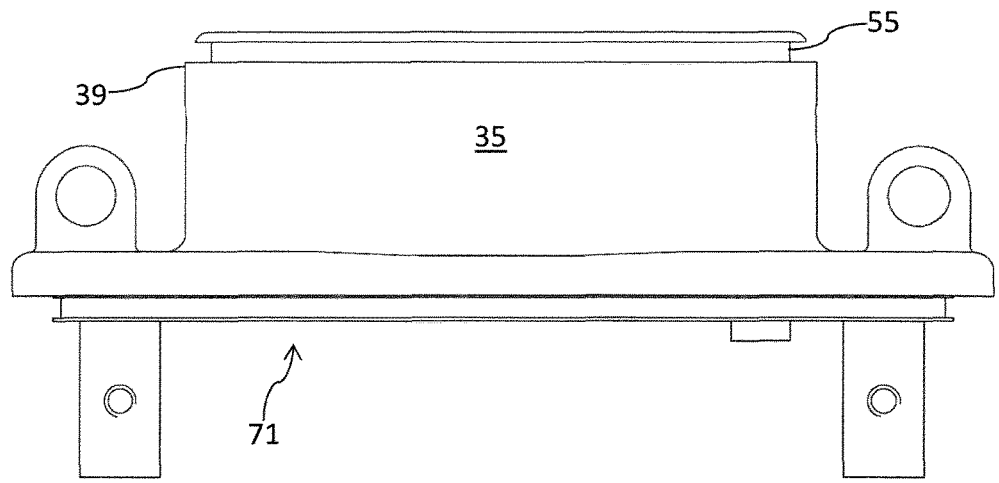
FIG. 3 is a side view of the collar without gasket.
Figure 4:
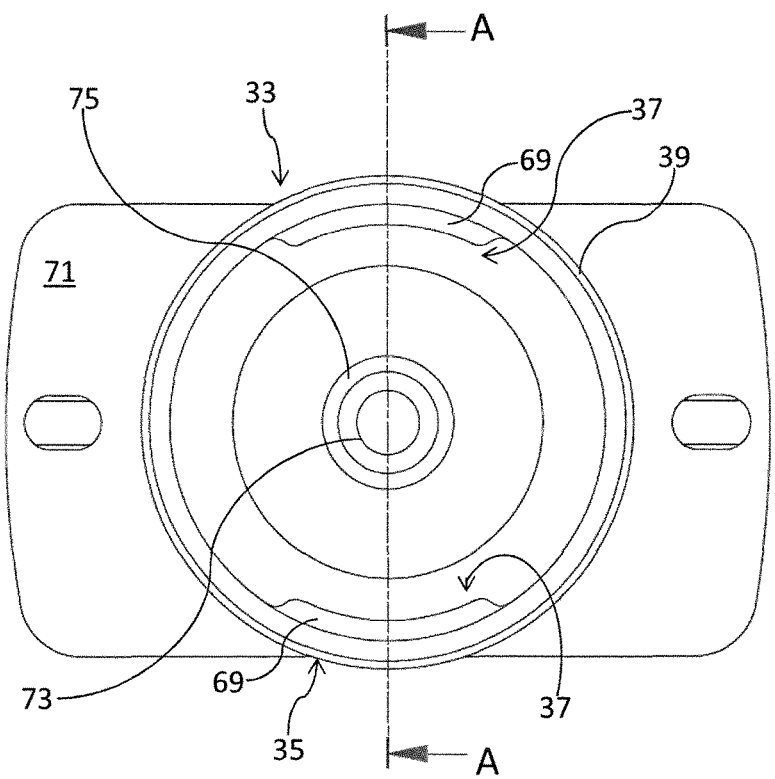
FIG. 4 is a top plan view of the collar shown in FIG. 3.
Figure 5:
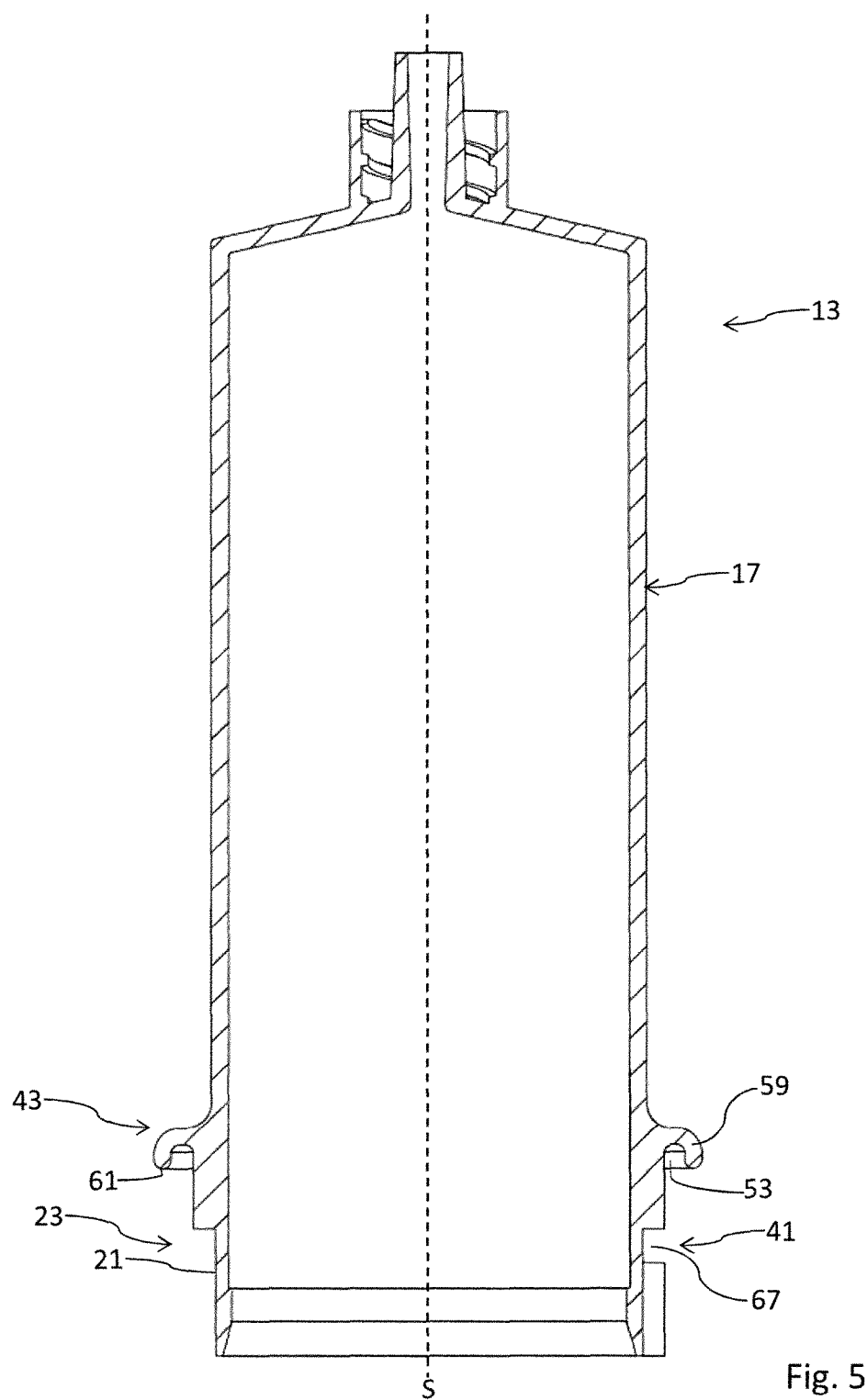
FIG. 5 is a longitudinal section of the syringe shown in FIG. 1.

In all Figures, equal or functionally equivalent parts have been denoted by the same reference numerals.

Referring to FIGS. 1 to 5, a first embodiment of the invention is shown, where the connecting arrangement is denoted in the whole by reference numeral 11. Connecting arrangement 11 enables the firm and reversible connection of a syringe 13 to a pump 15. Pump 15 is an electromechanical pump and allows drug infusion into the body of a living being by means of syringe 13.

Syringe 13 comprises a hollow cylindrical syringe body 17 having a first end, or front end, 19. Front end 19 is open and tapered for drug discharge. Preferably, said end 19 is externally equipped with a connecting element 19a, for instance of the "luer-lock" type, for connection of a cannula or outflow element (not shown), generally ending in a butterfly needle inserted into the body of the living being.

Hollow body 17 has a second open end 21, surrounded by connecting means 23 arranged to firmly connect syringe 13 to pump 15 in a removable manner.

A plunger 25 is housed within hollow body 17 and is axially slidable for causing suction and injection of the drug through front end 19 of the syringe.

Figure 6:
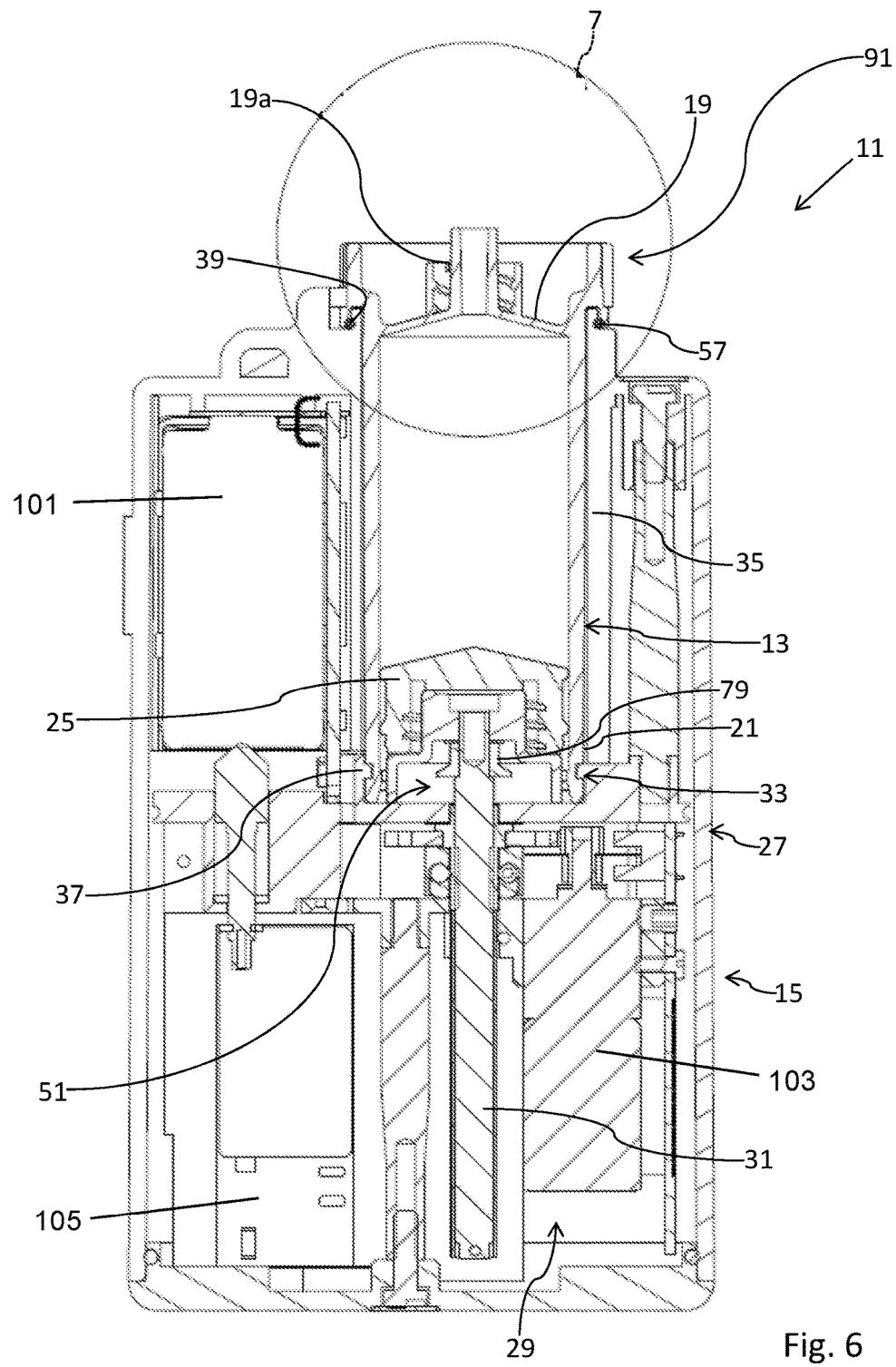
FIG. 6 is a longitudinal section of a pump equipped with a syringe connected to the pump through the arrangement of the invention, made in accordance with a second embodiment of the invention.
Figure 7:
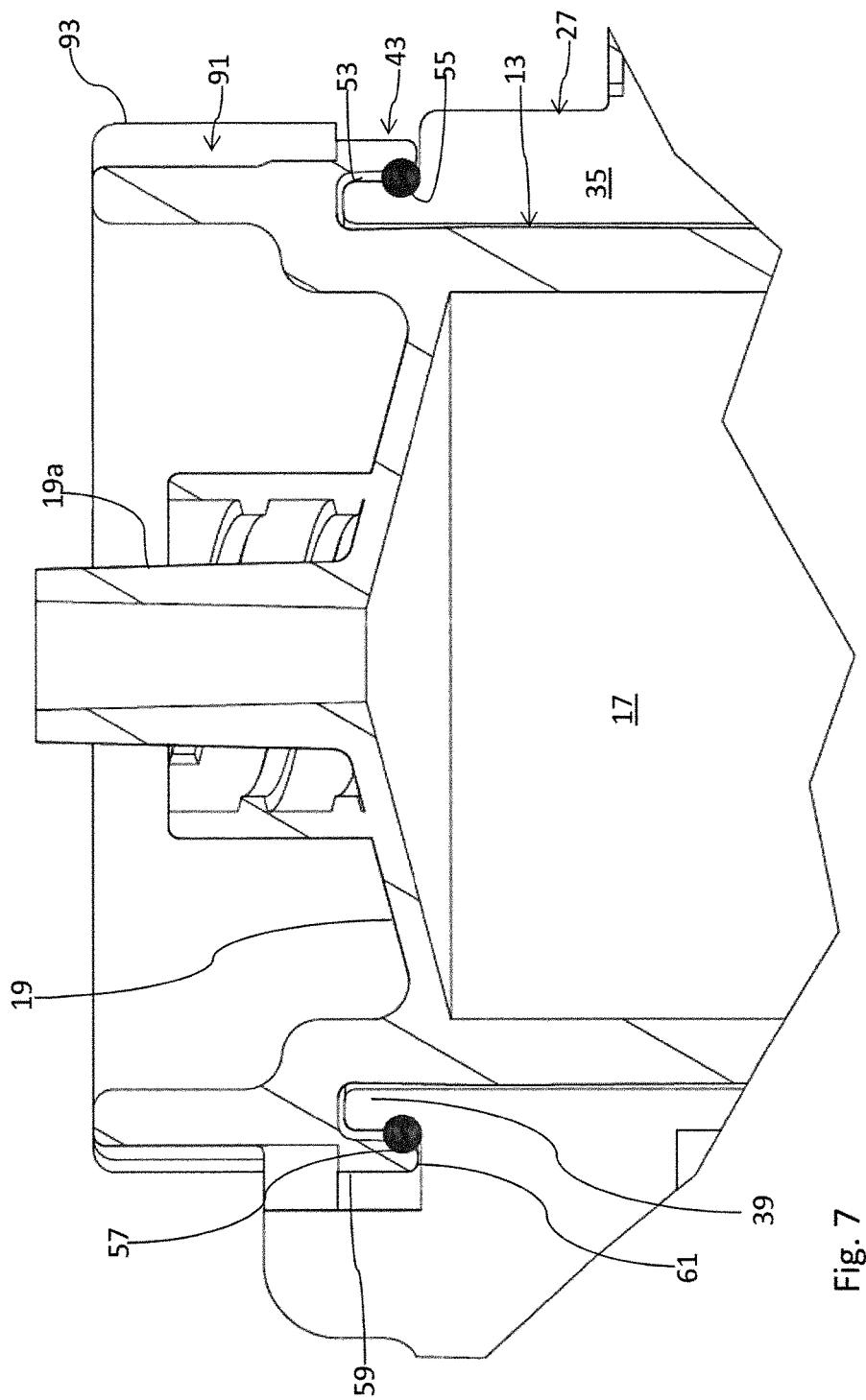
FIG. 7 is an enlarged view of a detail of FIG. 6.
Figure 8:
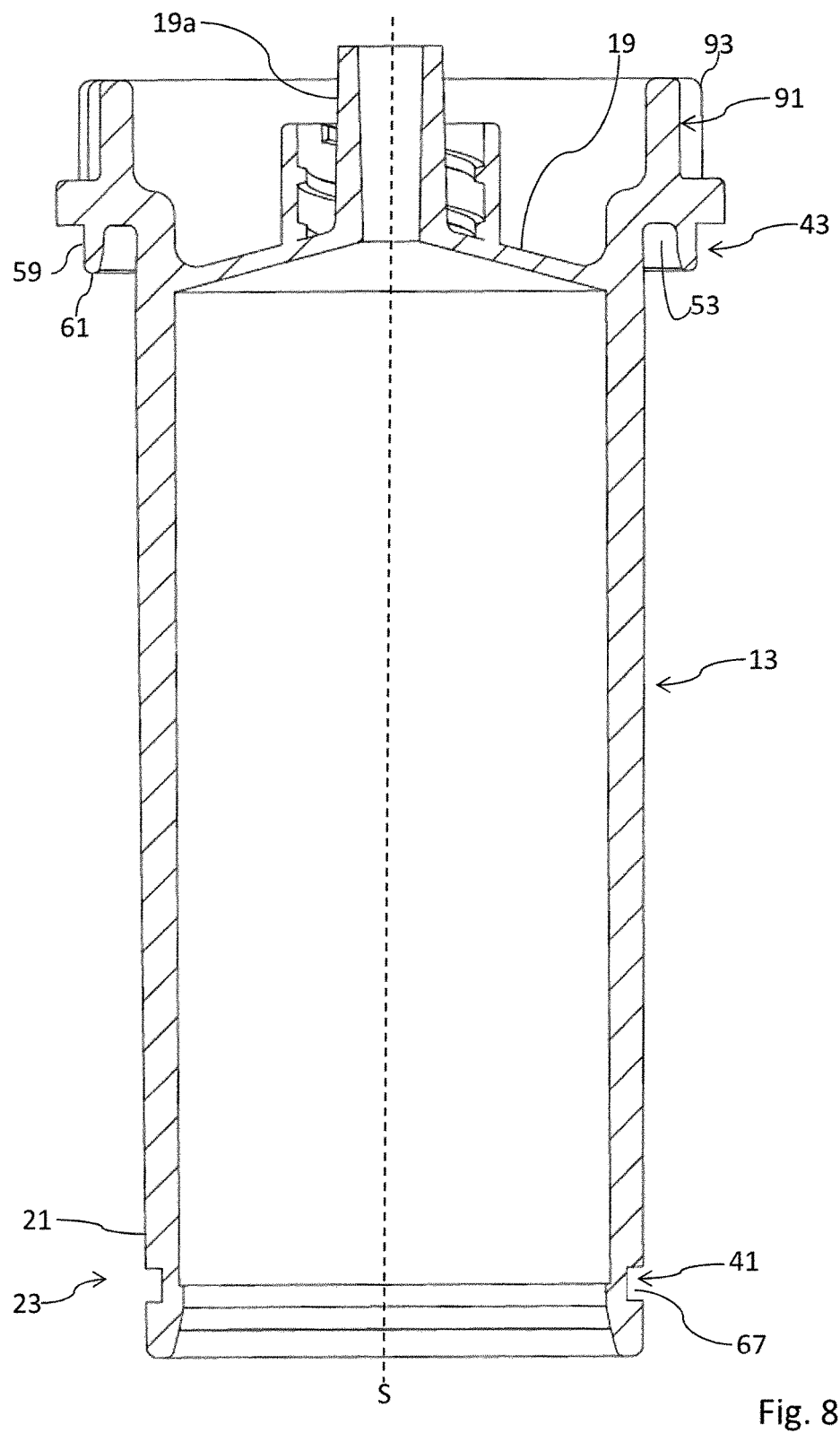
FIG. 8 is a longitudinal section of the syringe shown in FIG. 6.
Figure 9:
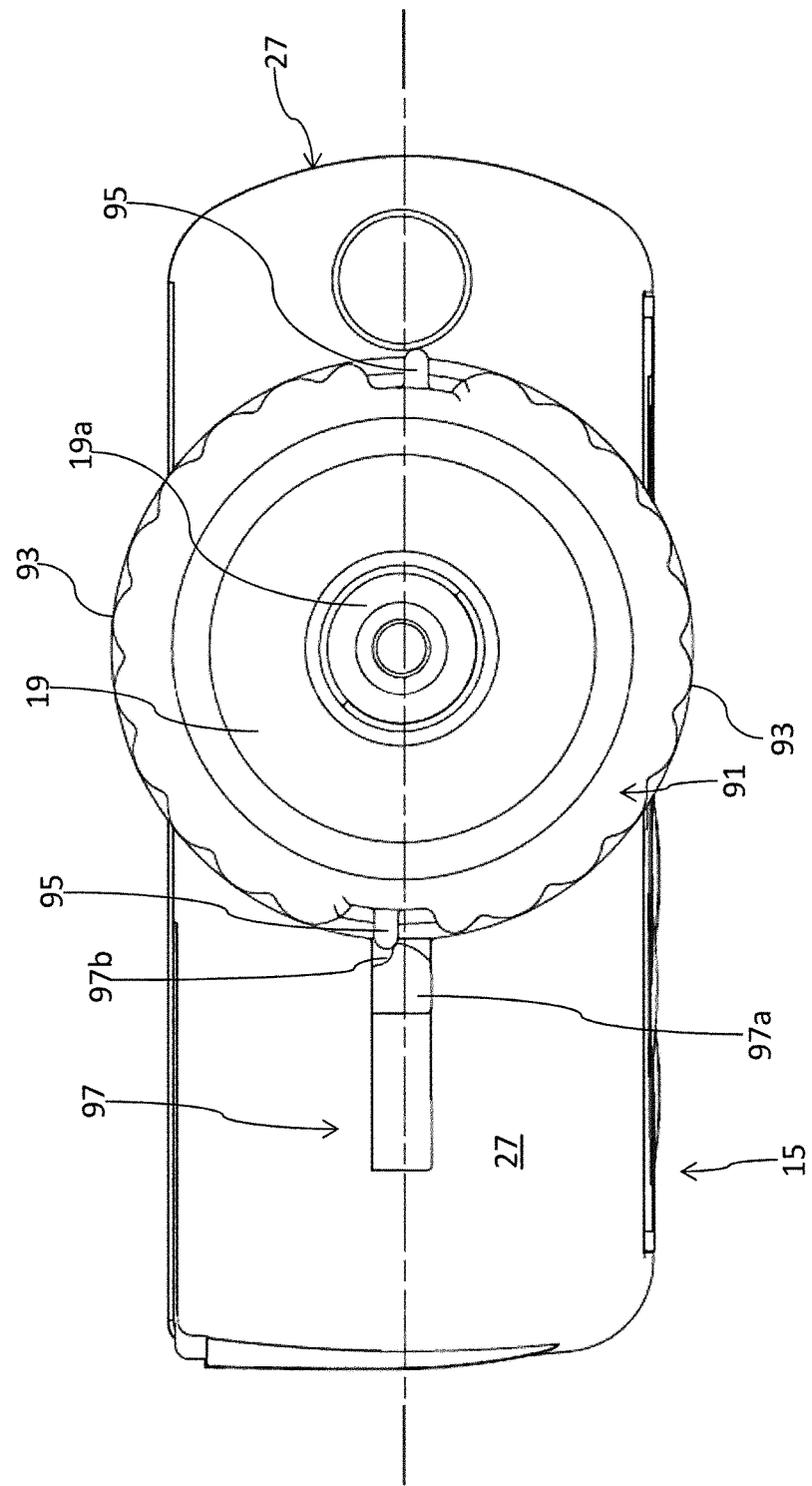
FIG. 9 is a top view of the pump shown in FIG. 6 equipped with a syringe.

Pump 15 comprises a pump body 27 internally housing electromechanical members 29 (refer to FIG. 6 for an example of structural details of electromechanical members 29). Said electromechanical members comprise a sliding rod 31 that partially projects out of pump body 27 in order to cause sliding of plunger 25 within body 17 of syringe 13 connected to pump 15.

Moreover, pump body 27 is externally provided with connecting means 33 arranged around sliding rod 31 and capable of receiving the second end 21 of syringe body 17 in an engaging configuration.

Advantageously, connecting means 33 externally provided on pump body 27 comprise a cylindrical collar 35 axially extending around sliding rod 31. Collar 35 defines a sealing end 39 and is internally provided with engaging elements 37.

Connecting means 23 surrounding the second end 21 of syringe body 17 comprise engaging elements 41 arranged to cooperate with engaging elements 37 provided in collar 35 for firmly connecting syringe 13 to pump 15 in a removable manner. Moreover, connecting means 23 surrounding the second end 21 of syringe body 17 comprise an annular flange 43 radially extending around syringe body 17 in a plane substantially perpendicular to axis "S" of syringe body 17.

Flange 43 is adapted to cooperate with sealing end 39 defined in collar 35 in order to establish a tight sealing between syringe body 17 and collar 35. Advantageously, thanks to the cooperation between flange 43 and sealing end 39, a substantially watertight condition is determined when syringe 13 is attached to pump 15. Consequently, any moisture that may be present in the surrounding environment outside pump 15 and syringe 13 attached thereto does not penetrate into pump body 27.

Sliding rod 31 is driven by electromechanical members 29 of the pump and has in its front part a pushing member 51 arranged to cooperate with plunger 25 of syringe 13. Pushing member 51 includes a cylindrical blind body 51a penetrating into the body of plunger 25, in a seat 25a provided therein.

In the embodiment illustrated, annular flange 43 radially extends around syringe body 17, in a plane substantially perpendicular to axis "S" of the syringe body.

In accordance with a preferred embodiment of the invention, flange 43 comprises a cross-section, i.e. a section lying in a plane parallel to axis "S" of syringe 13 when flange 43 is perpendicular to the axis of the syringe body, having the shape of an overturned "U" when syringe 13 is oriented with its front end 19 upwards. Consequently, an annular seat 53 adapted to receive sealing end 39 of collar 35 is defined in flange 43.

Always in accordance with a preferred embodiment of the invention, sealing end 39 of collar 35 comprises an annular groove 55 radially open towards the outside. Said groove 55 is adapted to receive a sealing gasket 57, e.g. an O-ring made of rubber or similar material. Annular groove 55 radially extends and the cross-section of gasket 57 is chosen so that said gasket 57 partially radially extends outside groove 55 for cooperating with the inner surface of outer wall 59 of annular seat 53 provided in flange 43.

Preferably, flange 43 comprises an outer wall 59 that, when syringe 13 is oriented with its front end 19 upwards, ends at its bottom with a rounded edge 61. Advantageously, thanks to such an arrangement, premature wear of sealing portion 39 and sealing gasket 57, if any, caused by the interference with flange 43 when syringe 13 is attached to or detached from pump 15, is avoided.

In accordance with a particular embodiment of the invention, collar 35 is provided with at least one radial channel 63 putting the inside of collar 35 in communication with the outside. Preferably, said channel 63 houses a porous element 65 made of a material suitable for allowing passage of air and preventing passage of moisture. Advantageously, in this manner, the pressure inside collar 35 is maintained equal to the pressure in the external environment, where atmospheric pressure typically exists. Preferably, two diametrically opposite channels 63 are provided.

Engaging elements 41 provided in connecting means 23 of syringe 13 and engaging elements 37 provided in connecting means 33 of pump 15 preferably comprise respective elements of a bayonet-type coupling 67, 69. Preferably, engaging elements 41 provided in the connecting means of syringe 13 are female elements, i.e. annular grooves 67 formed in the outer wall of syringe body 17, and engaging elements 37 provided in connecting means 33 of the pump are male elements, i.e. annular radial teeth 69 projecting inside collar 35. Preferably, two said engaging elements 37, 41 are provided, which are diametrically opposite and extend over an arc of circumference of about 30°.

In the embodiment illustrated, connecting means 33 of pump 15 are formed on a ferrule 71 closing one face of pump body 27. The base of ferrule 71 has an opening 73 for the passage of rod 31 partially projecting out of pump body 27 and extending outside in order to exert the push on plunger 51. A sleeve 75 is provided around opening 73 and it acts as an engaging element for a first end of an extensible bellows 77 surrounding rod 31. A second end of bellows 77 engages into a corresponding sleeve 79 provided inside pushing member 51. Said bellows 77 assists in protecting rod 31 and prevents liquids, e.g. the drug, from arriving in contact with rod 31 and penetrating into pump body 21, thereby negatively affecting the regular operation of pump 15.

Referring to FIGS. 6 to 9, a second embodiment of the invention is shown. In this embodiment, collar 35 substantially extends over the whole length of syringe 13. Consequently, flange 43 is defined in correspondence of front end 19. Advantageously, in accordance with this embodiment, syringe 13, when it is attached to pump 15, is substantially housed within collar 35.

In accordance with the invention, flange 43 is adapted to cooperate with sealing end 39 defined in collar 35 in order to establish a tight sealing between syringe body 17 and collar 35. Advantageously, thanks to the cooperation between flange 43 and sealing end 39, a substantially watertight condition is determined when syringe 13 is attached to pump 15. Consequently, any moisture that may be present in the surrounding environment outside pump 15 and syringe 13 attached thereto does not penetrate into pump body 27.

In the embodiment illustrated, annular flange 43 radially extends around syringe body 17, in a plane substantially perpendicular to axis "S" of the syringe body.

In accordance with this embodiment of the invention, flange 43 comprises a cross-section, i.e. a section lying in a plane parallel to the axis of syringe 13 when flange 43 is perpendicular to axis "S" of the syringe body, having the shape of an overturned "U" when syringe 13 is oriented with its front end 19 upwards. Consequently, an annular seat 53 adapted to receive sealing end 39 of collar 35 is defined in flange 43.

Always in accordance with this embodiment of the invention, sealing end 39 of collar 35 comprises an annular groove 55 radially open towards the outside. Said groove 55 is adapted to receive a sealing gasket 57, e.g. an O-ring made of rubber or similar material. Annular groove 55 radially extends and the cross-section of gasket 57 is chosen so that said gasket 57 partially extends radially outside groove 55 for cooperating with inner surface of outer wall 59 of annular seat 53 provided in flange 43.

Preferably, flange 43 comprises an outer wall 59 that, when syringe 13 is oriented with its front end 19 upwards, ends at its bottom with a rounded edge 61. Advantageously, thanks to such an arrangement, premature wear of sealing portion 39 and sealing gasket 57, if any, caused by the interference with flange 43 when syringe 13 is attached to or detached from pump 15, is avoided.

In this embodiment, pump 15 comprises a pump body 27 internally housing sliding rod 31 being part of electromechanical members 29 of pump 15. The electromechanical members 29 further include battery 101, electric motor 103, and printed circuit 105. In this embodiment, rod 31 remains therefore within collar 35 of pump body 27 during the sliding of plunger 25 caused by the sliding of rod 31.

In this embodiment, front end 19 of syringe 13 further comprises a second flange 91 provided with radial projections 93 making grip by the user easier. A pair of diametrically opposite teeth 95 is provided, radially projecting from the second flange 91. Teeth 95 are arranged to interfere with an abutment 97 provided in pump body 27 and having a curved end 97a, defining a stop edge 97b. Interference between one of teeth 95 and said end 97a determines the desired sensation of proper connection of syringe 13 to pump body 27 when syringe 13 is turned for being attached to the pump.

In the embodiment illustrated, the second flange 91 is adjacent to the first flange 43 and both flanges are integrated into syringe body 17.

Hollow body 17 of syringe 13 has a second open end 21 where engaging elements 41 are provided, arranged to cooperate with engaging elements 37 provided at the base of collar 35 for firmly connecting syringe 13 to pump 15 in a removable manner.

Engaging elements 41 provided in connecting means 23 of syringe 13 and engaging elements 37 provided in connecting means 33 of pump 15 preferably comprise respective elements of a bayonet-type coupling 67, 69. Preferably, engaging elements 41 provided in the connecting means of syringe 13 are female elements, i.e. annular grooves 67 formed in the outer wall of syringe body 17, and engaging elements 37 provided in connecting means 33 of the pump are male elements, i.e. annular radial teeth 69 projecting inside collar 35. Preferably, two said engaging elements 37, 41 are provided, which are diametrically opposite and extend over an arc of circumference of about 30°.

The connecting arrangement as described and illustrated can undergo several changes and modifications, falling within the same inventive principle.

We claim:

1. A connecting arrangement for connecting a syringe to an electromechanical pump for drug infusion,
   wherein the syringe comprises a hollow cylindrical syringe body having a first, tapered open end for discharging a drug and a second open end, said syringe body being surrounded by connecting means arranged to firmly connect the syringe to the pump in a removable manner, and an axially sliding plunger being housed in the syringe body for causing suction and injection of the drug through the first end;
   wherein the pump comprises a pump body housing electromechanical members comprising a sliding rod arranged to cause sliding of the plunger within the syringe body of the syringe connected to the pump, said pump body being provided with connecting means arranged to receive in an engaging configuration the syringe body;
   wherein the connecting means of the pump body comprises a cylindrical collar extending axially around the sliding rod and being internally provided with engaging elements, said collar defining a sealing end;
   wherein the connecting means surrounding the syringe body comprises engaging elements arranged to cooperate with the engaging elements of the collar for firmly connecting the syringe to the pump in the removable manner, and an annular flange extending radially around the syringe body, said annular flange being adapted to cooperate with the sealing end of the collar in order to establish a tight seal between the syringe body and the collar;
   wherein the annular flange defines an annular seat adapted to receive the sealing end of the collar, the annular seat being located within an overturned "U" shape in cross-section defined by the annular flange when the syringe is oriented with the first end upwards such that the annular flange has a laterally-extending wall that extends in a plane perpendicular to an axis of the syringe body and an outer longitudinally-extending wall that extends in a plane parallel to the axis of the syringe body; and
   wherein the sealing end of the cylindrical collar comprises a radially-outward opening annular groove in which a sealing gasket is seated such that a radially outermost portion of the sealing gasket extends outside the groove for cooperating with an inward-facing surface of the outer longitudinally-extending wall of the annular flange to form the tight seal;
   whereby, when the syringe is attached to the pump, any moisture that may be present in a surrounding environment outside the pump and the syringe attached thereto does not penetrate into the pump body.

2. The arrangement according to claim 1, wherein said sealing gasket comprises a rubber O-ring.

3. The arrangement according to claim 1, wherein the outer longitudinally-extending wall of the annular flange has a rounded free edge.

4. The arrangement according to claim 1, wherein the collar has at least one radial channel communicating an inside of the collar with an outside of the collar and wherein said at least one radial channel houses a porous element made of a material suitable for allowing passage of air and preventing passage of moisture.

5. The arrangement according to claim 1, wherein the engaging elements of the connecting means surrounding the syringe body and the engaging elements of the collar of the connecting means of the pump body comprise male/female elements, respectively, or vice versa, of a bayonet-type coupling.

* * * * *